US010369261B2

(12) United States Patent
Jonas et al.

(10) Patent No.: US 10,369,261 B2
(45) Date of Patent: Aug. 6, 2019

(54) METHOD AND DEVICE FOR SUPPLYING DIALYSIS LIQUID TO A DIALYSIS APPARATUS

(71) Applicant: FRESENIUS MEDICAL CARE DEUTSCHLAND GMBH, Bad Homburg (DE)

(72) Inventors: Jorg Jonas, Bogota (CO); Wolfgang Wehmeyer, Tubingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 153 days.

(21) Appl. No.: 15/521,307

(22) PCT Filed: Oct. 14, 2015

(86) PCT No.: PCT/EP2015/073792
§ 371 (c)(1),
(2) Date: Apr. 24, 2017

(87) PCT Pub. No.: WO2016/062593
PCT Pub. Date: Apr. 28, 2016

(65) Prior Publication Data
US 2017/0304519 A1 Oct. 26, 2017

(30) Foreign Application Priority Data
Oct. 25, 2014 (DE) .......... 10 2014 015 858

(51) Int. Cl.
*A61M 1/16* (2006.01)
*A61M 1/14* (2006.01)
(52) U.S. Cl.
CPC ............ *A61M 1/1656* (2013.01); *A61M 1/14* (2013.01); *A61M 1/1601* (2014.02);
(Continued)

(58) Field of Classification Search
CPC .... A61M 1/14; A61M 1/1601; A61M 1/1607; A61M 1/1613; A61M 1/1656;
(Continued)

(56) References Cited

U.S. PATENT DOCUMENTS

| 2012/0165718 A1 | 6/2012 | Herrenbauer et al. |
| 2013/0037485 A1 | 2/2013 | Wilt et al. |
| 2013/0276898 A1 | 10/2013 | Remkes et al. |
| 2014/0209520 A1 | 7/2014 | Koch et al. |

FOREIGN PATENT DOCUMENTS

| DE | 9320151 U1 | 4/1995 |
| DE | 10302691 B3 | 4/2004 |
| DE | 102009037917 A1 | 2/2011 |
| EP | 2564884 A1 | 3/2013 |

OTHER PUBLICATIONS

International Preliminary Report on Patentability issued in corresponding International Patent Application No. PCT/EP2015/073792 dated Apr. 25, 2017 (11 pages).
(Continued)

*Primary Examiner* — John Kim
(74) *Attorney, Agent, or Firm* — Kilyk & Bowersox, P.L.L.C.

(57) ABSTRACT

The invention relates to a method and to a device for supplying a dialysis device with dialysate, and to a dialysis device comprising a device for supplying the dialysis device with dialysate. For producing dialysate, a container 13 filled with a pulverulent dialysate concentrate K is provided, the amount of dialysate concentrate in the container being set in such a way that an amount of dialysate sufficient for a specified number of dialysis treatments can be produced using the dialysate concentrate. The method according to the invention and the device according to the invention make it possible to align the amount K2 of concentrate in the container 13 and the planned consumption amount, which is dependent on the prescription from the doctor and the
(Continued)

treatment parameters established by the machine. After the individual dialysis treatments have been carried out, it is continuously monitored whether the amount of concentrate is sufficient. It may be monitored whether the amount of concentrate is sufficient for the following treatment or for all treatments still to be carried out. If it is not sufficient, an alarm signal is generated. Otherwise, a control signal for initiating each of the next treatment cycles is generated.

20 Claims, 3 Drawing Sheets

(52) U.S. Cl.
CPC .......... *A61M 1/1607* (2014.02); *A61M 1/167* (2014.02); *A61M 1/1613* (2014.02); *A61M 1/1666* (2014.02); *A61M 1/1668* (2014.02); *A61M 2205/18* (2013.01); *A61M 2205/3379* (2013.01); *A61M 2205/50* (2013.01)

(58) Field of Classification Search
CPC .. A61M 1/1666; A61M 1/1668; A61M 1/167; A61M 2205/18; A61M 2205/3379; A61M 2205/50
See application file for complete search history.

(56) References Cited

OTHER PUBLICATIONS

International Search Report and Written Opinion issued in corresponding International Patent Application No. PCT/EP2015/073792 (with English translation of International Search Report) dated Jan. 12, 2016 (20 pages).

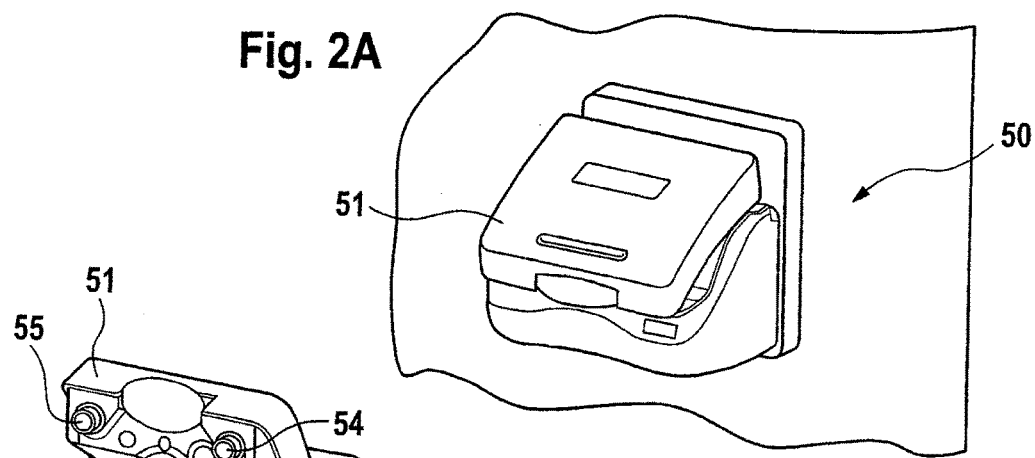
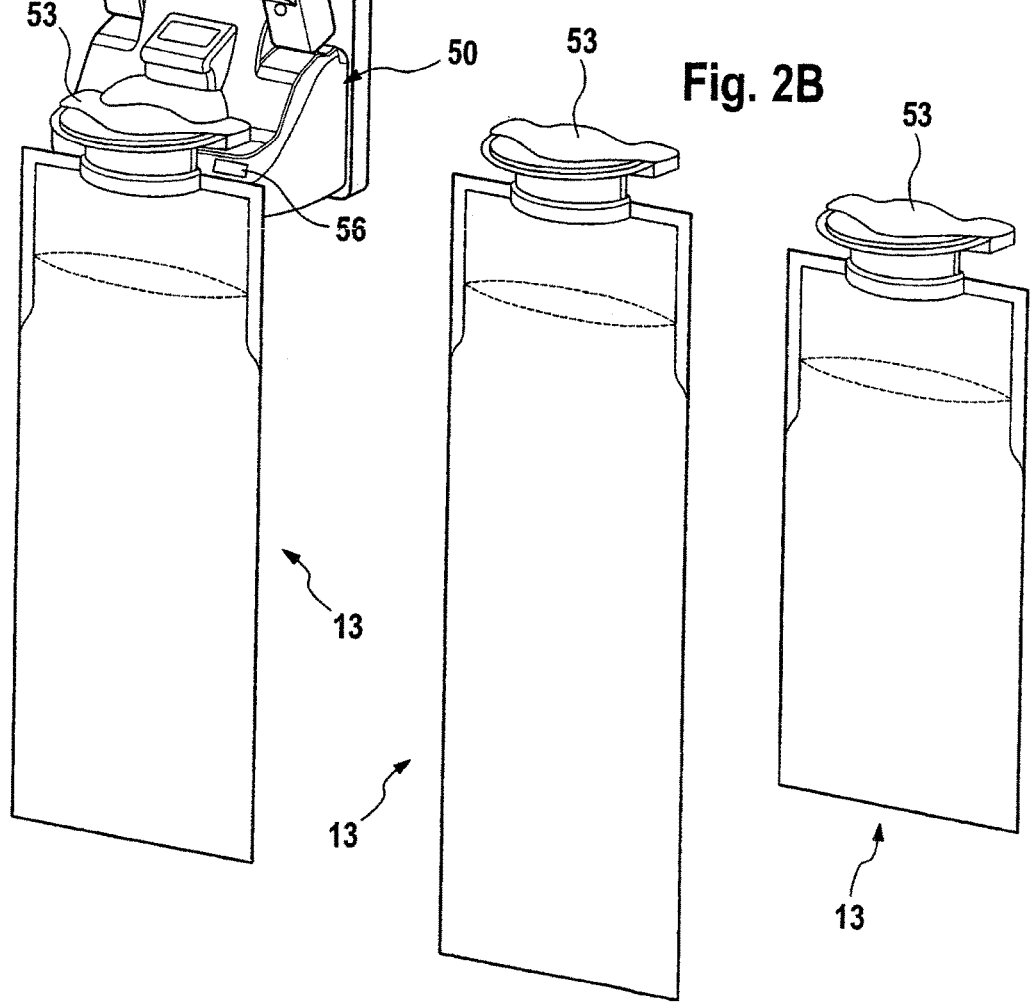

METHOD AND DEVICE FOR SUPPLYING DIALYSIS LIQUID TO A DIALYSIS APPARATUS

This application is a National Stage Application of PCT/EP2015/073792, filed Oct. 14, 2015, which claims priority to German Patent Application No. 10 2014 015 858.6, filed Oct. 25, 2014, which are incorporated in their entireties by reference herein.

The invention relates to a method and to a device for supplying a dialysis device with dialysate, and to a dialysis device comprising a device for supplying the dialysis device with dialysate.

During dialysis, the patient's blood flows continuously through the blood chamber of the dialyser, whilst dialysate flows constantly through the dialysate chamber. In order to produce dialysate, ready-made dialysate concentrates may be used, which are diluted with water in the dialysis devices. In dialysis centres, dialysate concentrates are either provided as a ready-made product in canisters, bags or cartridges, or are provided from a central tank via a circular line system.

Centrally provided dialysate concentrates are easy for the user to handle, but have the drawback that the dialysate cannot be—adapted individually to the requirements of the patient. Although locally provided concentrates make it possible to individually adapt the dialysate to the patient, they have to be brought to the dialysis device for each individual dialysis treatment.

In dialysis, in order to produce a liquid dialysis concentrate, bags or cartridges are used which are filled with a pulverulent dialysate concentrate. The concentrate bags or cartridges contain an amount of pulverulent dialysate concentrate sufficient for a single dialysis treatment. The bags or cartridges are filled with bicarbonate. Standard bicarbonate bags contain from 650 to 950 g of sodium carbonate. Initially, a liquid bicarbonate concentrate is produced from the pulverulent bicarbonate concentrate. In order to produce the dialysate, a further acid concentrate is required, which is provided in a canister or by means of a central supply. The bicarbonate concentrate and acid concentrate are subsequently mixed with water to form the finished dialysate.

The known concentrate bags comprising a pulverulent dialysate concentrate are only intended for single use for just one dialysis treatment. However, if in practice the ready-made dry concentrates provided for just one treatment are not used up, the residual amounts found in the bags after treatment have to be thrown away. It is only possible to dispose of the packaging materials correctly, by granulation or combustion, after completely emptying the bags.

DE 103 02 691 B3 discloses a device for supplying a dialysis device with dialysate, in which bicarbonate concentrate for dialysis treatment is provided in a container which is connected to the dialysis device. In the dialysis device, the pulverulent dialysate concentrate is mixed with water. A control and arithmetic unit calculates the dialysate rate to be set for the dialysis treatment in such a way that, after a specified treatment time has elapsed, a specified residual amount of dialysate concentrate or no residual amount of concentrate remains in the container.

The object of the invention is to provide a method by which it is possible to simplify the supply of a dialysis device with dialysate in accordance with requirements and to reduce production and transport costs. A further object of the invention is to provide a device by means of which it is possible to provide dialysate as required while simplifying handling and reducing production and transport costs.

Another object of the invention is to provide a dialysis device comprising a device for supplying the dialysis device with dialysate.

These objects are achieved by the features of the independent claims. The dependent claims relate to advantageous embodiments of the invention.

The method according to the invention and the device according to the invention are based on providing a ready-made dialysate concentrate in a container intended for single use, which container contains an amount of concentrate sufficient for a plurality of treatment cycles that are to be carried out in succession within a specified time period. The dialysate concentrate is preferably a pulverulent dialysate concentrate which is provided as a dry concentrate. However, the concentrate may also be liquid. The container may be of various configurations. Preferably, the container is a bag or cartridge. The specified time period within which the treatment cycles are to be carried out may be of various lengths. Preferably, the time period is one day on which a plurality of dialysis treatments are carried out so that the container contains the total requirement of concentrate for one day of dialysis.

The individual treatment cycles each comprise a preparation phase, preceding the dialysis treatment, for preparing the dialysis treatment and a treatment phase for carrying out the actual dialysis treatment, the amount of dialysate concentrate provided for one treatment cycle comprising a specified amount of dialysate concentrate for the preparation phase and a specified amount of dialysate concentrate for the treatment phase.

The preparation phase may be composed of a test phase, which is generally compulsory, and an optional cleaning phase, in which specific amounts of dialysate concentrate are used up. During the treatment phase, dialysate concentrate is used up to produce the dialysis solution. For the treatment, it may also be necessary to provide dialysate concentrate in order to produce a substitution solution for pre- or post-dilution. In the following, a dialysis solution and a substitution solution are also referred to as a dialysate.

If a plurality of containers having different fill volumes are provided, a container containing the amount of dialysate concentrate sufficient for the number of treatment cycles to be carried out one after the other within the specified time period can be selected from the available containers. Thus, the number of dialysis treatments to be carried out for example on one dialysis day is not limited to a particular number of treatments. The individual containers preferably differ only in fill volume such that they are interchangeable and do not require different connections to the dialysis device. For example, bags or cartridges comprising an amount of dialysate concentrate for three or four treatments on one day, preferably three treatments, may be provided. The maximum number of treatments using one container is determined by the time limit for tolerable germ growth in the container, which can be determined by the manufacturer and stored in the dialysis device as a safety parameter.

The container, for example for three dialysis treatments on one day of dialysis, is connected to the dialysis device. Whilst the container is connected to the dialysis device for the specified time period, the dialysate is produced for the individual treatment cycles using the particular partial amount of dialysate concentrate. The container is only removed from the dialysis device after the specified number of dialysis treatments has been carried out.

Providing the entire requirement of dialysate concentrate for a day of dialysis in just one container greatly reduces the number of handling steps, from unpacking the containers, through internal transport within the dialysis centre, to connecting the containers to the dialysis devices and throwing away the containers after carrying out the dialysis treatments. Since the container remains connected to the dialysis device on the day of dialysis, the sequence between the individual treatments on the day of dialysis can be accelerated. The method according to the invention thus allows for a more rapid overall sequence of the dialysis treatments on one day of dialysis. The more rapid overall sequence ultimately leads to savings on time and costs.

The production and transport costs for providing dialysate concentrate are reduced, since less-primary packaging material needs to be provided and transported. Furthermore, the costs of disposing of the containers and any remaining residual amount of dialysate concentrate that has not been used up are reduced. As a result, optimum use is made of the resources of dialysate concentrate and water during the treatments. The method according to the invention can be carried out automatically and without intervention by the operating personnel.

The method according to the invention and the device according to the invention provide that treatment parameters for each treatment cycle of the specified number of treatment cycles are inputted using an input unit. The treatment parameters may comprise patient-specific treatment parameters, for example the dialysis dose specified by the doctor, and machine-specific treatment parameters, for example the blood flow rate or dialysate rate. On the basis of the inputted treatment parameters, for each treatment cycle of the specified number of treatment cycles, a provided amount of dialysate concentrate is determined using an arithmetic and evaluation unit. The individual amounts of concentrate for the individual patients may be determined in accordance with various aspects. It is irrelevant to the invention how the individual amounts of concentrate are determined by the arithmetic and evaluation unit. The only key factor is that the amounts of concentrate are automatically specified by the arithmetic and evaluation unit, taking into account inputted treatment parameters.

The method according to the invention and the device according to the invention make it possible to align the amount of concentrate in the container and the planned consumption amount, which is dependent on the prescription from the doctor and the treatment parameters established by the machine, before treatment is carried out. For this purpose, the difference between the amount of dialysate concentrate in the container and the amount of dialysate concentrate provided for the specified number of treatment cycles is calculated. If the amount of dialysate concentrate in in the container is less than the amount of dialysate concentrate provided for the specified number of treatment cycles, an alarm signal which can trigger an optical and/or acoustic and/or tactile alarm is generated. In this connection, an alarm is understood to mean any event which informs the user that the amount of concentrate is insufficient. The user can subsequently select a different container having a larger fill volume. The planned amount of concentrate and the residual amount present for the subsequent treatments can also be displayed to the user.

By contrast, if the amount of dialysate concentrate in in the container is not less than the amount of dialysate concentrate provided for the specified number of treatment cycles, a control signal is generated. In this connection, a control signal is understood to mean any signal which can initiate the first treatment cycle.

It is thus ensured that the dialysis treatments can only take place if a sufficient amount of concentrate is available. If there is an excess of dialysate concentrate, the method according to the invention and the device according to the invention provide that the excess is subdivided among different aspects. However, the aim is that no dialysate concentrate or only a specific residual amount of concentrate remains in the container after all treatment cycles have been carried out.

In one embodiment, any excess of dialysate concentrate is used up in the final treatment cycle such that the container is completely emptied or a small residual volume remains in the container as a buffer. In this way, the dialysis dose for the final patient can be increased. In an alternative embodiment, before the treatment cycles are carried out, the concentrate excess is distributed across all planned treatment cycles. The distribution may be in even parts or in accordance with a specified individual weighting, for example on the basis of the individual amounts of concentrate specified for the patients. Thus, all of the treatments benefit from a larger amount of concentrate, which is associated with a higher dialysis dose.

After the individual dialysis treatments have been carried out, it is continuously monitored whether the amount of concentrate is sufficient. It can be monitored whether the amount of concentrate is sufficient for the next treatment or for all treatments still to be carried out. It can also be monitored whether the amount of concentrate is sufficient for the next treatment and for all of the treatments. If this is not the case, an alarm signal for generating an alarm is generated once again. Otherwise, a control signal for initiating the particular next treatment cycle is generated once again.

Between the individual treatment cycles, it is continuously monitored whether the amount of dialysate concentrate actually used up corresponds to the planned amount of concentrate, so as to be able to determine the actual amount of concentrate for the treatments still to be carried out, which amount is determined by the difference between the amount of concentrate located in the container beforehand and the amount of concentrate actually used up.

The amount of dialysate concentrate in in the container before the treatment cycles are carried out can be detected automatically by the arithmetic and evaluation unit or can be inputted by the medical staff using the input unit. The invention provides different variants. The selected container, for example the bag or cartridge, which differs from the other containers in fill volume, can be detected automatically by way of a specific identification feature. For electrical identification, the known (RFID) transponders may be used. However, the data may also be recorded using a capacitive sensor. Optical identification is possible using the known barcodes. Mechanical identification can be carried out by detecting the outlines of the containers or by detecting further identifying features such as edges, locking elements or pins. Furthermore, it is possible to determine the amount of dialysate concentrate in in the container using gravimetric weight measurement. Further, it is possible to pneumatically detect the fill amount by determining the fill volume of the container using water up to a fixed pressure point.

The dialysis device according to the invention, which has a device for supplying the dialysis device with dialysate, may have a dialysate system which makes it possible to carry out a disinfection or cleaning phase between the individual dialysis treatments. In a preferred embodiment, the dialysate is also produced during the disinfection or cleaning phase. In this embodiment, the dialysate system comprises a first portion, which includes the dialysis chamber of a dialyser subdivided into a blood chamber and the dialysate chamber by a semipermeable membrane, and a second portion, which includes a unit for producing dialysate from the dialysate concentrate. Furthermore, the dialysis device comprises a unit for disinfecting the dialysate system, the first and second portions of the dialysate system being formed as separable portions such that, in the event of separation, liquid located in one portion cannot enter the other portion. The separation of the dialysate system makes it possible to carry out the routine required for producing the dialysate at the same time as disinfection of the dialysis device such that the entire method sequence for producing the dialysate or for disinfection need not be completely stopped between the treatment cycles, also saving time. Since the hydraulic part for preparing the dialysate is separated from the disinfection process, the disinfection process can also be shortened.

To separate the portion of the dialysate system in which the dialysate is produced from the dialysate concentrate, various means may be provided, for example one or more blocking members, check valves or the like.

The dialysis device may comprise a control unit for the unit for disinfecting the dialysate system, which control unit is configured in such a way that, during the disinfection of the dialysis device, the means for separating the portion of the dialysate system are actuated in such a way that the portion of the dialysate system in which the dialysate is produced from the dialysate concentrate is partitioned off during the disinfection of the dialysis device. The control unit is configured in such a way that, during the disinfection of the dialysis device, the unit for producing dialysate carries out a routine required for producing the dialysate in the separate portion of the dialysate system in which the dialysate is produced from the dialysate concentrate.

For disinfection, a hot disinfection method may be carried out at a high temperature using pure osmosis water so as to be able to completely and safely remove chemical residues in dead spaces between disinfected and non-disinfected parts of the dialysate system. For local decalcification, rinsing may be carried out between the individual dialysis treatments using an acid concentrate. Calcification of the machine can be prevented by suitable measures, for example by using citrate as a strong acid in the acid concentrate or by limiting the concentration of bicarbonate depending on the admixture of acetate in the finished dialysate.

BRIEF DESCRIPTION OF THE DRAWINGS

In the following, embodiments of the method according to the invention and of the device according to the invention are described in greater detail with reference to the drawings, in which:

FIG. 2A shows a unit for connecting a container, which is filled with a dialysate concentrate, to the dialysis device of FIG. 1 in order to carry out a plurality of treatment cycles, FIG. 2B shows the unit for connecting the container of FIG. 2A, to which a container for carrying out a plurality of treatment cycles is connected.

Figure 1:
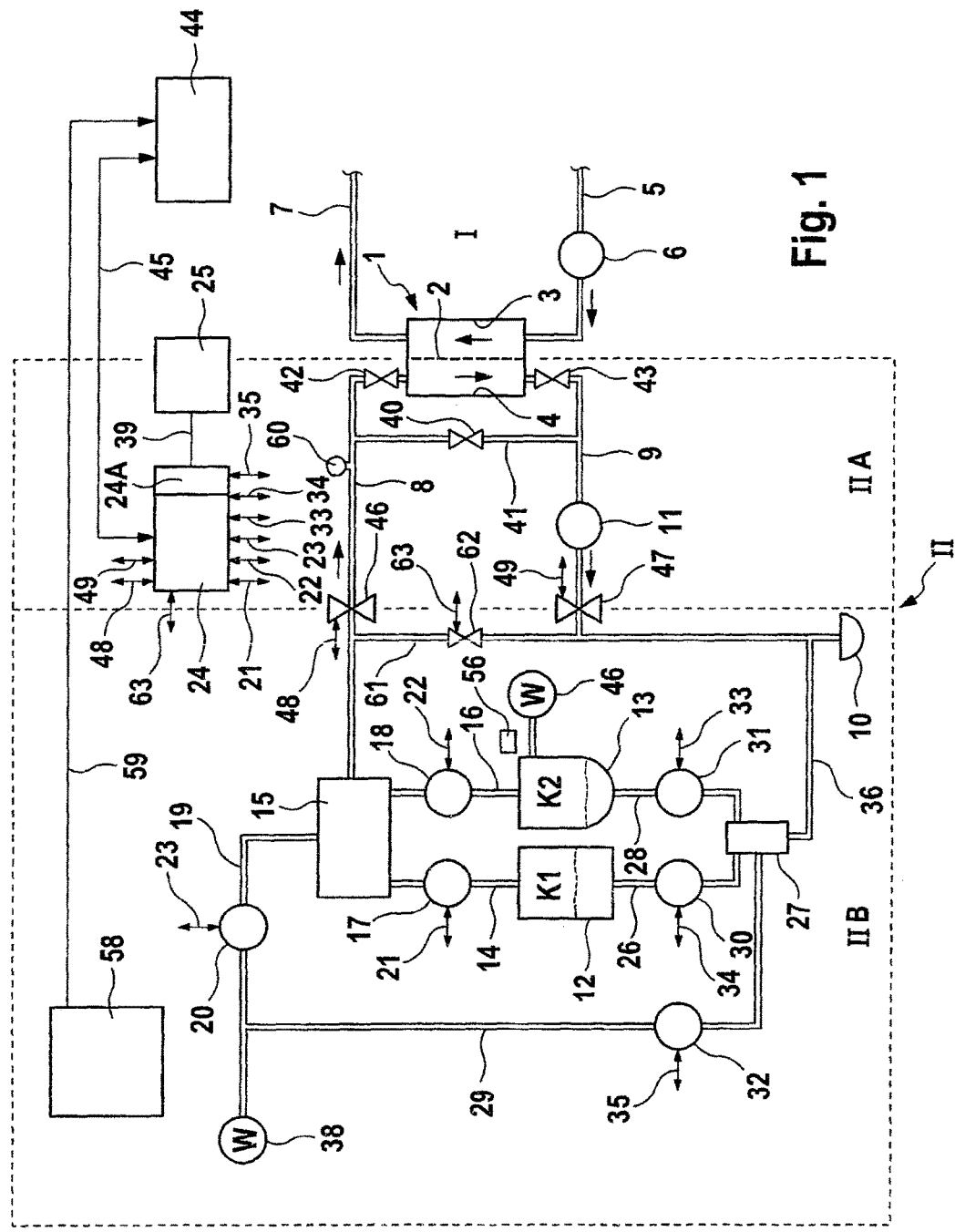
FIG. 1 is a simplified schematic view of an embodiment of the dialysis device according to the invention.

The haemodialysis device comprises a dialyser 1, which is subdivided into a blood chamber 3 and a dialysate chamber 4 by a semipermeable membrane 2. The inlet of the blood chamber 3 is connected to one end of a blood supply line 5, into which a blood pump 6 is connected, whilst the outlet of the blood chamber is connected to one end of a blood discharge line 7. A dialysate supply line 8 leads to the inlet of the dialysate chamber 4, and a dialysate discharge line 9 proceeds from the outlet of the dialysate chamber and leads to a drain 10. A dialysate pump 11 is connected into the dialysate discharge line 9. During the dialysis treatment, the patient's blood flows through the blood chamber 3 of the dialyser 1, whilst dialysate flows through the dialysate chamber 4 in counterflow. The semipermeable membrane 2 of the dialyser 1 separates the extracorporeal blood circuit I of the dialysis device from the dialysate system II.

The device for supplying the dialyser 1 with dialysate is preferably a component of the dialysis device. However, it may also form a separate unit. In the following, the supply device is described in detail.

In order to produce the dialysate, two concentrates K1, K2 are mixed with water W in a specified volume ratio.

The supply device has two units each for connecting a container, one container being a canister 12, which in the present embodiment is filled with acid concentrate. The other container is a bag 13, which in the present embodiment is filled with sodium bicarbonate as a dry concentrate.

A first concentrate line 14 proceeds from the canister 12 and leads to a mixing chamber 15, and a second concentrate line 16 proceeds from the bag 13 and leads to the mixing chamber 15. A proportioning pump 17, 18 is connected into the first and second concentrate lines 14, 16, respectively. A water line 19, which is connected to a water source 38, further leads to the mixing chamber 15. A proportioning pump 20 is likewise connected into the water line 19.

The proportioning pumps 17, 18 and 20 are connected via data and control lines 21, 22 and 23 to an arithmetic and evaluation unit 24 of the supply device, which specifies particular conveyance rates for the proportioning pumps such that the concentrates K1 and K2 and the water are each mixed in the mixing chamber 15 in a specified volume ratio to produce the dialysate. On the bag 13 comprising the dry concentrate, a water connection 46 is provided for supplying a specified amount of water.

So as to obtain from the dry concentrate a liquid concentrate to be mixed with water in a specified volume ratio, the powder is initially dissolved in water, which flows into the bag 13 from the water connection 46. By supplying water, a saturated solution is produced from the pulverulent dialysate concentrate. The saturated solution may be produced in a continuous process. The volume of the liquid dialysate concentrate produced from the pulverulent dialysate concentrate is determined by the amount of pulverulent dialysate concentrate and the volume of the supplied water, the machine parameters setting a specified ratio of the amount of pulverulent dialysate concentrate to the volume of the supplied water.

A drainage line 26 proceeds from the canister 12 and leads to a second mixing chamber 27, whilst a second drainage line 28 proceeds from the bag 13 and leads to the mixing chamber 27. A water line 29 proceeds from the water source 38 and likewise leads to the mixing chamber 27. Pumps 30, 31, 32 are connected into the first and second drainage lines 26, 28 and the water line 29, respectively, and are connected to the arithmetic and evaluation unit 24 via control lines 33, 34, 35. A drain line 36 proceeds from the mixing chamber 27 and leads to the drain 10.

The supply device further has an input unit 25, which communicates with the arithmetic and evaluation unit 24 via a data line 39. Various treatment parameters, determined by the doctor's prescription and by treatment parameters set by the machine, can be inputted at the input unit 25. The doctor may for example specify a dialysis dose by inputting the blood flow, dialysate flow and treatment time for a particular dialyser 1 using the input unit 25. The doctor can also prescribe pre-dilution or post-dilution at a specified flow rate for the substituate. A profile may also be inputted for the dialysate flow. However, other methods known to a person skilled in the art are also possible for estimating the volume required to achieve a particular dialysis dose. The amount of substituate can for example be determined from the blood volume to be treated, it being possible for example for the total infusion volume to be 30% of the blood volume in post-dilution and 60% in pre-dilution. The blood volume can in turn be calculated from the specified blood flow rate and the actual blood flow determined therefrom and the specified treatment time.

In order to interrupt the dialysis treatment, for example if complications occur or for carrying out a test or other routines for preparing the dialysis treatment, a bypass line 41, into which a bypass valve 40 is connected, and a check valve 42 that is upstream of the dialysate chamber 4 and a check valve 43 that is downstream of said dialysate chamber of the dialyser 1 may be provided. If the dialysis treatment is interrupted, the dialysate flows through the bypass line 40 into the drain 10, without dialysate flowing through the dialysate chamber 4.

The dialysis device has a central arithmetic and control unit 44, which communicates via a data line 45 with the arithmetic and evaluation unit 24 of the supply device. However, the arithmetic and evaluation unit 24 of the supply device may also be a component of the central arithmetic and control unit 44 of the dialysis device. Further units may be provided, for example a balancing unit, but are not shown in FIG. 1.

To produce the dialysate to be supplied to the dialyser 1, the control and arithmetic unit 24 specifies the conveyance rates of the proportioning pumps 17, 18, 20 in such a way that in the mixing chamber 15 the concentrates K1, K2 are each mixed with water in the specified volume ratio.

The dialysate is for example to be produced from the dialysate concentrate available in the container 13 for three treatment cycles, which are to follow one another on a day of dialysis.

A treatment cycle is composed of an obligatory test phase and an optional cleaning phase as well as the actual treatment phase. During the cleaning phase, the production of the dialysate can proceed with a low dialysate flow. However, the production of the dialysate can also be interrupted during the cleaning phase. During the treatment, the production of dialysate as a substitution solution may be required if the doctor has prescribed pre-dilution or post-dilution.

As a result, the amount of dialysate required for a treatment cycle is composed of the amount of dialysate concentrate for the obligatory test phase $V_{Test}$, the amount of dialysate concentrate for the optional cleaning phase $V_{Clean}$, and the amount of concentrate for the treatment phase $V_{Treat}$.

The amount $V_{Treat}$ of concentrate to be provided for the treatment phase may be subdivided into an amount $V_{Dial}$ of concentrate for providing the dialysis solution (obligatory) and an amount $V_{Sub}$ of concentrate for providing the substitution solution (optional) for pre-dilution or post-dilution. In the present embodiment, $V_{Test}$ and $V_{Clean}$ are treatment parameters stored in the dialysis machine. $V_{Test}$ is determined by the arithmetic and evaluation unit 24 in accordance with the doctor's prescription on the basis of the treatment parameters inputted using the input unit 25.

During an initial test phase, the control and arithmetic unit 44 of the dialysis device can close the check valves 42, 43 and open the bypass valve 41 so that the dialysate flows through the bypass line 40 into the drain 10 for a predetermined time interval $T_{test}$. The dialysate rate is for example $Qd_{test}$. Subsequently, after the specified time interval $T_{test}$ has elapsed, the actual dialysis treatment can begin. During the dialysis treatment, a specified dialysate rate Qd may be set. If a complication occurs during the dialysis treatment, the dialyser 1 can be separated and the dialysate can be discarded via the drain 10 via the bypass 40. If faults occur frequently, it may be necessary to extend the treatment accordingly so as to achieve the effective treatment time $T_{eff}$.

Furthermore, the dialysis device has a unit 58 for disinfecting the dialysate system II, which unit is merely shown in outline in FIG. 1. The disinfection unit 58 is connected to the central control unit 44 of the dialysis device via a control line 59. Disinfection devices of this type are part of the prior art. For disinfection, the disinfectant, for example hot water, is supplied via a connector 60 of the dialysate supply line 8, the connectors of the dialyser 1 being short-circuited using a short-circuit piece (not shown).

Standard disinfection of the dialysis devices includes the mixing chamber 15. However, the method according to the invention provides a modification of the cleaning method and of the dialysis device, since the container 13 remains connected to the dialysis device between the treatment cycles.

The dialysate system II of the dialysis device comprises a first portion IIA, which includes the dialysate chamber 4 of the dialyser 1, and a second portion IIB, which includes the unit consisting of the above-disclosed components for producing the dialysate. The two portions IIA and IIB can be interconnected and partitioned off from one another. To separate the second portion IIB, in which the dialysate is produced, suitable means are provided, which may for example be blocking members 46, 47, arranged in the dialysate supply line 8 and dialysate discharge line 9 and connected to the control and arithmetic unit 24 via control lines 48, 49. However, these blocking members are merely shown for illustrative purposes. Furthermore, a bypass line 61, comprising a bypass valve 62 which is connected to the arithmetic and evaluation unit 24 via a control line, is provided between the dialysate supply line 8 and the dialysate discharge line 9.

During the cleaning phase, in which the check valves 46 and 47 are closed, the bypass valve 62 is open, the production of the dialysate not being interrupted. The dialysate, which can be produced at as low a liquid rate as possible, is thrown away via the bypass line 61.

The device according to the invention is intended for carrying out a plurality of, in other words at least two, treatment cycles within a specified time period, for example a day of dialysis, using only one container 13 filled with an amount $M_0$ of a pulverulent dialysate concentrate sufficient for the specified number x of treatment cycles. It is assumed here that the other container 12, in which the acid concentrate is provided, also contains an amount of concentrate sufficient for the specified number of dialysis treatments.

FIG. 2A shows the unit 50 for connecting the container 13 filled with the pulverulent dialysate concentrate. The connecting unit 50 comprises a shutter 51, which is closed in the position shown in FIG. 2A. To connect the concentrate container 13, the shutter 51 is opened. FIG. 2B shows the connecting unit 50 with an open shutter 51.

In the present embodiment, the concentrate container 13 is a bag filled with a dry concentrate, in particular bicarbonate. However, the concentrate container may also be a cartridge. The concentrate bag 13 comprises a connector piece 52, by means of which the bag can be suspended on the connecting unit 50 when the shutter 51 is open. On the underside, the shutter 51 comprises an inflow connector 54 for water and an outflow connector 55 for the liquid dialysate concentrate, by means of which a connection to the bag interior can be established when the shutter 51 is closed.

Figure 2C:
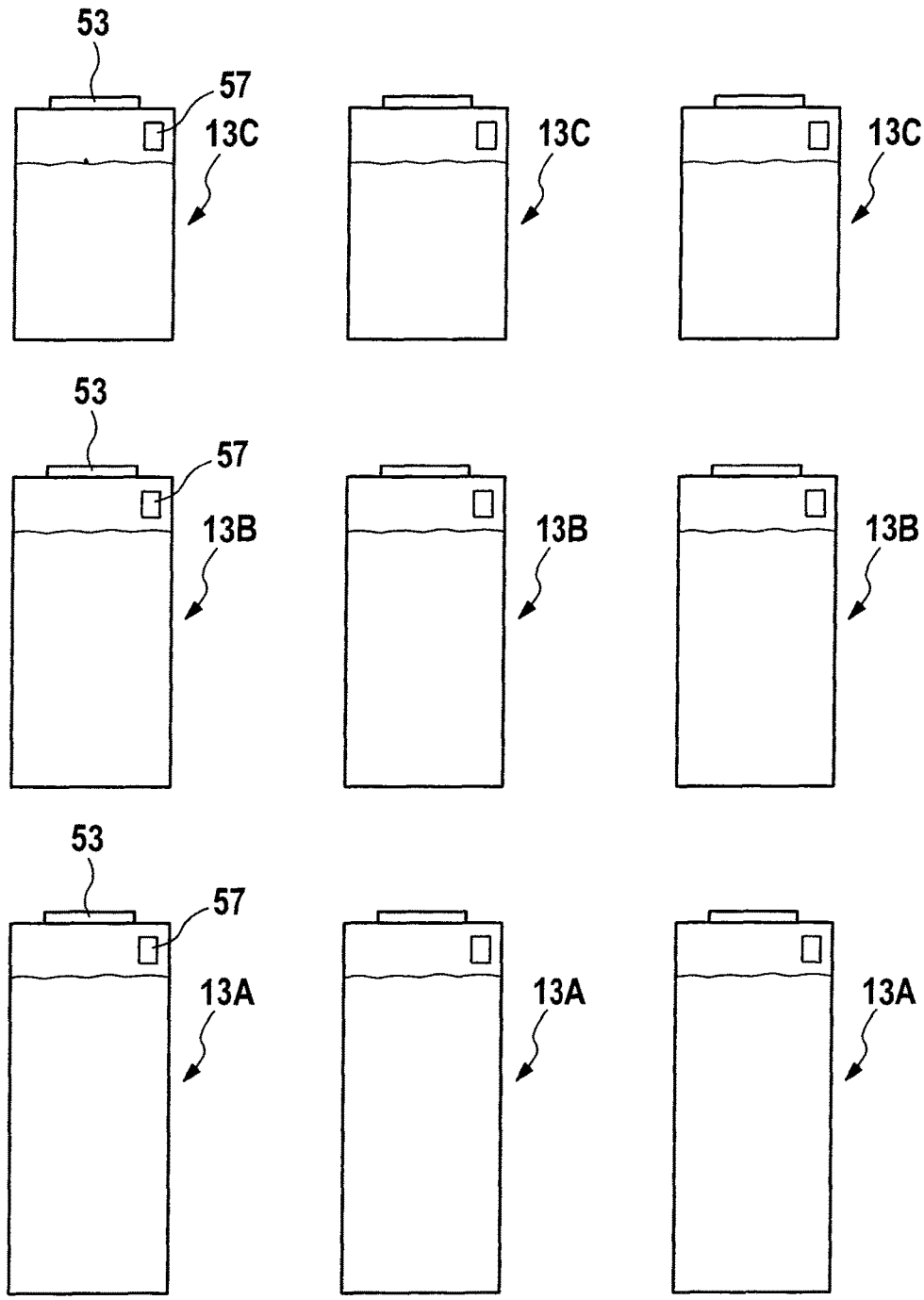
FIG. 2C is a schematic view of a stock of containers, each intended for a plurality of treatment cycles.

In order to carry out the treatment cycles on one day of dialysis, a plurality of concentrate bags 13 of this type are provided, which differ only in bag size and fill volume. FIG. 2C shows a plurality of identical concentrate bags 13A filled with an amount of bicarbonate sufficient for example for 4 dialysis treatments, and a plurality of identical bags 13B for 3 treatments and a plurality of bags 13C for just 2 treatments. Previously established averages for the concentrate consumption per treatment cycle are used as a basis for setting the amount of concentrate in the bags.

For carrying out a plurality of treatment cycles on one day of dialysis, a concentrate bag 13 is selected which contains the necessary amount $M_0$ of dialysate concentrate. For one day of dialysis comprising x treatment cycles (x=1-4), for example comprising 3 treatment cycles, the concentrate bag 13B containing bicarbonate for the number of treatment cycles, for example 3 cycles, is selected. This concentrate bag 13B is subsequently connected to the connecting unit 50 of the dialysis device.

The treatment parameters specified for the treatment, for example the dialysis dose, blood flow rate, dialysate rate and substitution rate are inputted using the input unit 24.

The supply device has a unit 56 (only shown schematically) for identifying the concentrate bag 13B as a bag intended for a specified number of treatment cycles, in other words a bag for 3 treatment cycles. In the present example, the unit 56 for identifying the bag is an optical read unit for a barcode 57 located on the bag. However, it is also possible to input the specified number of treatment cycles using the input unit 25.

The arithmetic and evaluation unit 24 is configured in such a way that it carries out the following method steps. For this purpose, the arithmetic and evaluation unit 24 may comprise a data processing unit on which a data processing program (software) runs.

The arithmetic and evaluation unit 24 calculates the concentrate consumption per cycle $V_1, V_2 \ldots V_x$ to be expected on the basis of the treatment parameters inputted using the input unit 25:

$$V_1 = V_{Test} + V_{Treat} + V_{Clean(optional)} \quad \text{(treatment parameter for cycle 1)}$$

$$V_2 = V_{Test} + V_{Treat} + V_{Clean(optional)} \quad \text{(treatment parameter for cycle 2)}$$

$$\ldots$$

$$V_x = V_{Test} + V_{Treat} + V_{Clean(optional)} \quad \text{(treatment parameter for cycle x)}$$

In the present embodiment, the following amounts of concentrate are determined for the 3 treatment cycles:

$$V_1 = V_{Test} + V_{Treat} + V_{Clean(optional)} \quad \text{(treatment parameter for cycle 1)}$$

$$V_2 = V_{Test} + V_{Treat} + V_{Clean(optional)} \quad \text{(treatment parameter for cycle 2)}$$

$$V_3 = V_{Test} + V_{Treat} + V_{Clean(optional)} \quad \text{(treatment parameter for cycle 3)}$$

Thereupon, the arithmetic and evaluation unit 24 calculates the difference between the amount $M_0$ of dialysate concentrate in in the container 13 and the amount $V_1+V_2+V_3 \ldots +V_x$ of dialysate concentrate provided for the specified number x=3 of treatment cycles:

$$V = V_1 + V_2 + V_3 \ldots + V_x$$

In the embodiment, $V=V_1+V_2+V_3$ is calculated. If the amount $M_0$ of dialysate concentrate in the container is less than the amount V of dialysate concentrate provided for the specified number of treatment cycles, an alarm signal for generating an alarm is generated. By contrast, a control signal for initiating the first treatment cycle is generated if the amount $M_0$ of dialysate concentrate in the container is not less than the amount V provided for the specified number of treatment cycles. The control unit 44 of the dialysis device receives the alarm signal and the control signal of the supply device. If an alarm signal is generated, an optical and/or acoustic and/or tactile alarm is provided. For example, it is displayed to the medical staff on a display unit 24A of the arithmetic and evaluation unit 24 that the amount of concentrate is not sufficient. The amount $M_0$ of concentrate in the container and the required amount V of concentrate may also be displayed on the display unit 24A.

When the control unit 44 has received the control signal, the first treatment cycle, for which the amount $V_1$ of concentrate is available, begins.

In practice, the amount of concentrate provided for the treatment cycle may deviate from the amount of concentrate actually used up. After the first treatment x=1 has been carried out and before the second treatment cycle x=2 is carried out, the arithmetic and evaluation unit 24 monitors whether the residual volume of dialysate concentrate available for the treatment cycles still to be carried out is sufficient for the second and third treatment cycles. Initially, the amount $V_{1,actual}$ of dialysate concentrate actually used up is determined, and, from the difference between the amount $M_0$ of dialysate concentrate in the container before the first treatment cycle was carried out and the amount $V_{1,actual}$ of concentrate actually used up in the first cycle, the residual amount $M_1$ of dialysate concentrate in the container still available for the second and third treatment cycles is calculated:

$$M_1 = M_0 - V_{1,actual}$$

If the residual amount $M_1$ of dialysate concentrate is less than the amount $V_2+V_3$ of dialysate concentrate provided for the second and third treatment cycles, an alarm signal is generated. By contrast, if the residual amount $M_1$ is not less than the amount provided for the second and third treatment cycles, a control signal for initiating the second treatment cycle is generated.

After the second treatment cycle x=2 has been carried out and before the third treatment cycle x=3 is carried out, the arithmetic and evaluation unit 24 determines the amount $V_{2,actual}$ of dialysate concentrate actually used up in the second treatment cycle, and calculates the residual amount of dialysate concentrate $M_2$ still actually available for the third treatment cycle:

$$M_2 = M_1 - V_{2,actual}$$

The arithmetic and evaluation unit 24 monitors whether the amount $M_2$ of concentrate is sufficient for the third treatment cycle x=3. If $M_2$ is less than $V_3$, an alarm signal is generated, and if $M_2$ is not less than $V_3$, a control signal for initiating the third treatment cycle is generated.

In practice, before the final treatment cycle is carried out, an excess of dialysate concentrate which is not required for the final treatment will occur.

For the embodiment, the concentrate excess $M_R$ is calculated:

$$M_R = M_2 - V_3$$

If the residual amount $M_R$ of dialysate concentrate is greater than the amount $V_3$ of dialysate concentrate provided for the final treatment cycle, the dialysis device is controlled in such a way that the residual amount of dialysate concentrate is completely used up in the final treatment cycle or a specified residual amount of dialysate concentrate remains in the container. For example, a constant dialysate rate may be set in such a way that the residual amount is used up to the greatest possible extent. However, a corresponding profile for the dialysate rate may also be predetermined. Thus, the dialysis dose for the final patient is increased. However, the dialysis dose cannot be reduced for all patients.

An alternative embodiment provides monitoring, after the individual treatment cycles have been carried out, whether the amount of concentrate still in the container is sufficient not for all treatment cycles still to be carried out, but merely for the next treatment. As a result, an alarm signal is generated if the residual amount of dialysate concentrate is less than the amount of dialysate concentrate provided for the following treatment cycle, and a control signal is generated if the residual amount of dialysate concentrate is not less than the amount of dialysate concentrate provided for the following treatment cycle.

In the embodiment, for example, after the first treatment cycle x=1 has been carried out and before the second treatment cycle x=2 is carried out, it is monitored whether the residual volume of dialysate concentrate available for the treatment cycles still to be carried out is sufficient for the second treatment cycle. For this purpose, the amount $V_{1,actual}$ of dialysate concentrate actually used up is determined, and the residual amount $M_1$ of dialysate concentrate in the container, which residual amount of dialysate concentrate is still available for the second and third treatment cycles, is calculated:

$$M_1 = M_0 - V_{1,actual}$$

If the residual amount $M_1$ of dialysate concentrate is less than the amount $V_2$ of dialysate concentrate provided for the second treatment cycle, an alarm signal is generated. Otherwise, a control signal for initiating the second treatment cycle is generated.

In a further alternative embodiment, the control and evaluation unit 24 is configured in such a way that, before the treatment cycles are carried out, the amount $M_0$ of dialysate concentrate in the container is subdivided among the specified number x of treatment cycles, each of the treatment cycles being allocated a specified amount $V_1'$, $V_2'$, $V_3'$ ... $V_x'$ of dialysate concentrate that is set in such a way that, after the treatment cycles have been carried out, a specified residual amount $M_R$ or no residual amount of dialysate concentrate remains in the container.

After the amounts $V_1$, $V_2$ ... $V_x$ of concentrate provided for the individual treatment cycles have been determined, the amount $M_0$ of dialysate concentrate available in the container is subdivided in such a way that, after the final cycle, $M_0$ is completely or almost completely used up. The subdivision of the amounts of concentrate among the cycles (x=1-4) may be in equal parts $M_0/x$ or in percent in accordance with the provided concentrate consumption $V_1$, $V_2$ ... $V_x$, resulting in the amount of concentrate available for each cycle:

$V_2'$ ... $V_x'$, with the proviso $V_1' \geq V_1; V_2' \geq V_2; \ldots V_x' \geq V_x$ and $V_1' + V_2' + \ldots V_x' = M_0$ or $V_1' + V_2' + \ldots V_x' = M_0 - M_k$ Thus, a larger amount of dialysate concentrate is available for each treatment cycle such that the dialysis dose is increased for all patients. However, if in fact more dialysate concentrate to be used up than is provided, an alarm is given.

In the present embodiment, the following amounts of concentrate are determined for the 3 treatment cycles:

$V_1 = V_{Test} + V_{Treat} + V_{Clean(optional)}$  (treatment parameter for cycle 1)

$V_2 = V_{Test} + V_{Treat} + V_{Clean(optional)}$  (treatment parameter for cycle 2)

$V_3 = V_{Test} + V_{Treat} + V_{Clean(optional)}$  (treatment parameter for cycle 3)

$V_1', V_2', V_3'$, with the proviso $V_1' \geq V_1; V_2' \geq V_2; V_3' \geq V_3$ and $V_1' + V_2' + V_3' = M_0$ or $V_1' + V_2' + V_3' = M_0 - M_k$ The dialysis device is controlled in such a way that the amount $V_1'$ of dialysate concentrate specified for the first treatment cycle is used up. For this purpose, a constant dialysate rate may be adapted accordingly or the profile may be altered accordingly.

After the first treatment cycle using the amount $V_1'$ of dialysate concentrate specified for the first treatment cycle, before the start of the second treatment cycle using the amount $V_2'$ of concentrate, the amount $V_{1,actual}$ of dialysate concentrate actually used up in the first treatment cycle is determined so as to calculate the residual volume of dialysate concentrate available for the second and third treatment cycles from the difference between the amount of dialysate concentrate in the container and the amount of dialysate concentrate actually used up in the first treatment cycle.

The residual volume of dialysate concentrate available for each of the treatment cycles still to be carried out is now again subdivided among the number of treatment cycles still to be carried out, the treatment cycles again each being allocated a specified amount $V_1''$, $V_2''$, $V_3''$ ... $V_x''$ of dialysate concentrate that is set in such a way that, after the treatment cycles have been carried out, a specified residual amount $M_k$ or no residual amount of dialysate concentrate remains in the container. This subdivision of the dialysate concentrate takes place successively up to the final treatment cycle. In the embodiment, after the first cycle the residual amount of concentrate is subdivided between the second and third cycle, in other words the amount of concentrate provided for the second and third cycles is increased by the remaining excess. After the second treatment cycle, the residual amount is subsequently available for the third cycle.

The described method steps are carried out successively until all treatments on the day of dialysis are complete. The concentrate bag 13B remains connected to the dialysis device until all treatments are complete. Only at the end of the day of dialysis is the bag removed, it already being possible at this time to connect a new bag to the connecting unit for the next day of dialysis.

While the concentrate bag 13B is connected to the dialysis device, the dialysis device is disinfected between the individual dialysis treatments. For this purpose, the disinfection unit 58 is set in operation, the blocking members 56 and 47 in the dialysate supply line 8 and the dialysate discharge line 9 being closed. As a result, disinfection only takes place in the first portion IIA of the dialysate system II. In the second portion IIB of the dialysate system I, the dialysate for the following treatment is prepared while the disinfection routine is being carried out so that the following treatment can begin immediately after the end of the disinfection routine. Disinfection of the entire dialysate system only takes place at the end of the day of dialysis such that the dialysis device is immediately ready for operation again on the next day of dialysis.

The invention claimed is:

1. Method for supplying a dialysis device with dialysate, comprising the following method steps:
    providing a container (13) that is intended for single use and is filled with a dialysate concentrate (K2) for producing dialysate, wherein the amount ($M_0$) of dialysate concentrate in the container is set in such a way that it is possible to use the dialysate concentrate to produce an amount of dialysate sufficient for a specified number (x) of treatment cycles,
    inputting treatment parameters for each treatment cycle of the predetermined number (x) of treatment cycles using an input unit (24A),
    determining a provided amount ($V_1$, $V_2$, $V_3$, ... $V_x$) of dialysate concentrate for each treatment cycle of the specified number (x) of treatment cycles on the basis of the inputted treatment parameters using an arithmetic and evaluation unit (24),
    calculating the difference in the amount ($M_0$) of dialysate concentrate in the container and the amount ($V_1+V_2+V_3 \ldots +V_x$) of dialysate concentrate provided for the specified number (x) of treatment cycles, wherein
    an alarm signal for generating an alarm is generated if the amount ($M_0$) of dialysate concentrate in the container is less than the amount ($V_1+V_2+V_3 \ldots +V_x$) of dialysate concentrate provided for the specified number (x) of treatment cycles, and
    a control signal for initiating the first treatment cycle is generated if the amount ($M_0$) of dialysate concentrate in the container is not less than the amount of dialysate concentrate provided for the specified number (x) of treatment cycles ($V_1+V_2+V_3 \ldots +V_x$).

2. Method for supplying a dialysis device according to claim 1, characterised in that, after the first treatment has been carried out using the amount ($V_1$) of dialysate concentrate provided for the first treatment cycle and before the start of each subsequent treatment cycle using the amount ($V_1$, $V_2$, $V_3$, ... $V_x$) of dialysate concentrate provided for the relevant subsequent treatment cycle,
    the amount ($V_{actual}$) of dialysate concentrate actually used up in the preceding treatment cycle is determined,
    the residual volume of dialysate concentrate available for the treatment cycles still to be carried out is calculated from the difference between the amount of dialysate concentrate in the container before the preceding treatment was carried out and the amount of dialysate concentrate actually used up in the preceding treatment cycle, and
    an alarm signal for an alarm is generated if the residual amount of dialysate concentrate is less than the amount of dialysate concentrate provided for the treatment cycles still to be carried out, and
    a control signal for initiating the following dialysis treatment is generated if the residual amount of dialysate concentrate is not less than the amount of dialysate concentrate provided for the treatment cycles still to be carried out.

3. Method for supplying a dialysis device according to claim 1, characterised in that, after the first treatment cycle has been carried out using the amount ($V_1$) of dialysate concentrate provided for the first treatment cycle and before the start of each subsequent treatment cycle using the amount ($V_1$, $V_2$, $V_3$, ... $V_x$) of dialysate concentrate provided for each of the subsequent treatment cycles,
    the amount ($V_{actual}$) of dialysate concentrate actually used up in the preceding treatment cycle is determined,
    the residual volume of dialysate concentrate available for the treatment cycles still to be carried out is calculated from the difference between the amount of dialysate concentrate in the container before the preceding treatment cycle was carried out and the amount of dialysate concentrate actually used up in the preceding treatment cycle, and
    an alarm signal for an alarm is generated if the residual amount of dialysate concentrate is less than the amount of dialysate concentrate provided for the following treatment cycle, and
    a control signal for initiating the following dialysis treatment is generated if the residual amount of dialysate concentrate is not less than the amount of dialysate concentrate provided for the following treatment cycle.

4. Method for supplying a dialysis device according to claim 2, characterised in that, if the residual amount of dialysate concentrate is greater than the amount of dialysate concentrate provided for the final treatment cycle, the dialysis device is controlled in such a way that the residual amount of dialysate concentrate is used up in the final treatment cycle or a predetermined residual amount of dialysate concentrate remains in the container.

5. Method for supplying a dialysis device according to claim 1, characterised in that, before the treatment cycles are carried out, the amount ($M_0$) of dialysate concentrate in the container is subdivided among the specified number (x) of treatment cycles, the treatment cycles each being allocated a specified amount ($V_1'$, $V_2'$, $V_3'$ ... $V_x'$) of dialysate concentrate that is set in such a way that, after the treatment cycles have been carried out, a specified residual amount or no residual amount of dialysate concentrate remains in the container.

6. Method for supplying a dialysis device according to claim 5, characterised in that the dialysis device is controlled in such a way that the amount ($V_1'$) of dialysate concentrate specified for the first treatment cycle is used up.

7. Method for supplying a dialysis device according to claim 6, characterised in that, after the first treatment cycle has been carried out using the amount ($V_1'$) of dialysate concentrate specified for the first treatment cycle and before the start of each subsequent treatment cycle using the amount of dialysate concentrate specified for the relevant subsequent treatment cycle,
    the amount ($V_{actual}$) of dialysate concentrate actually used up in the preceding treatment cycle is determined,
    the residual volume of dialysate concentrate available for the treatment cycles still to be carried out is calculated from the difference between the amount of dialysate concentrate in the container before the preceding treatment cycle was carried out and the amount of dialysate concentrate actually used up in the preceding treatment cycle, and
    the residual volume of dialysate concentrate available for each of the treatment cycles still to be carried out is subdivided among the number of treatment cycles still to be carried out, the treatment cycles each being allocated a specified amount ($V_1''$, $V_2''$, $V_3''$ ... $V_x''$) of dialysate concentrate that is set in such a way that, after the treatment cycles have been carried out, a specified residual amount or no residual amount of dialysate concentrate remains in the container.

8. Method for supplying a dialysis device according to claim 7, characterised in that an alarm signal for generating an alarm is generated if the residual volume of dialysate concentrate available for each of the treatment cycles still to be carried out is less than the amount of dialysate concentrate specified for the treatment cycles still to be carried out, and a control signal for initiating the following treatment cycle is generated if the residual volume of dialysate concentrate available for each of the treatment cycles still to be carried out is not less than the amount of dialysate concentrate specified for the treatment cycles still to be carried out.

9. Method for supplying a dialysis device according to claim 1, characterised in that the treatment cycle comprises a preparation phase, preceding the dialysis treatment, for preparing the dialysis treatment and a treatment phase for carrying out the dialysis treatment, the amount of dialysate concentrate provided for a treatment cycle comprising a specified amount of dialysate concentrate for the preparation phase and a specified amount of dialysate concentrate for the treatment phase.

10. Device for supplying a dialysis device with dialysate, comprising a connecting unit (50) for connecting a container (13) that is intended for single use and is filled with a dialysate concentrate (K2) for producing dialysate, wherein the amount ($M_0$) of dialysate concentrate in the container is set in such a way that it is possible to use the dialysate concentrate to produce an amount of dialysate sufficient for a specified number (x) of treatment cycles can be, an input unit (24A) for inputting treatment parameters for each treatment cycle of the specified number (x) of treatment cycles, an arithmetic and evaluation unit (24), configured in such a way that an amount ($V_1, V_2, V_3, \ldots V_x$) of dialysate concentrate provided for the treatment cycle is determined for each treatment cycle of the specified number (x) of treatment cycles on the basis of the inputted treatment parameters, the difference between the amount ($M_0$) of dialysate concentrate in the container and the amount ($V_1+V_2+V_3 \ldots +V_x$) of dialysate concentrate provided for the specified number (x) of treatment cycles is calculated, wherein an alarm signal for generating an alarm is generated if the amount ($M_0$) of dialysate concentrate in the container is less than the amount ($V_1+V_2+V_3 \ldots +V_x$) of dialysate concentrate provided for the specified number of treatment cycles, and a control signal for initiating the first treatment cycle is generated if the amount ($M_0$) of dialysate concentrate in the container is not less than the amount ($V_1+V_2+V_3 \ldots +V_x$) of dialysate concentrate provided for the specified number of treatment cycles.

11. Device for supplying a dialysis device with dialysate according to claim 10, characterised in that the arithmetic and evaluation unit (24) is configured in such a way that after the first treatment cycle has been carried out using the amount of dialysate concentrate provided for the first treatment cycle and before the start of each subsequent treatment cycle using the amount of dialysate concentrate provided for each of the subsequent treatment cycles, the amount ($V_{actual}$) of dialysate concentrate actually used up in the preceding treatment cycle is determined, the residual volume of dialysate concentrate available for the treatment cycles still to be carried out is calculated from the difference between the amount of dialysate concentrate in the container before the preceding treatment cycle was carried out and the amount of dialysate concentrate actually used up in the preceding treatment cycle, and an alarm signal for an alarm is generated if the residual amount of dialysate concentrate is less than the amount of dialysate concentrate provided for the treatment cycles still to be carried out, and a control signal for initiating the following dialysis treatment is generated if the residual amount of dialysate concentrate is not less than the amount of dialysate concentrate provided for the treatment cycles still to be carried out.

12. Device for supplying a dialysis device with dialysate according to claim 10, characterised in that the arithmetic and evaluation unit (24) is configured in such a way that after the first treatment cycle has been carried out and before the start of each subsequent treatment cycle, the amount ($V_{actual}$) of dialysate concentrate actually used up in the preceding treatment cycle is determined, the residual volume of dialysate concentrate available for the treatment cycles still to be carried out is calculated from the difference between the amount of dialysate concentrate in the container before the preceding treatment cycle was carried out and the amount of dialysate concentrate actually used up in the preceding treatment cycle, and an alarm signal for an alarm is generated if the residual amount of dialysate concentrate is less than the amount of dialysate concentrate provided for the following treatment cycle, and a control signal for initiating the following dialysis treatment is generated if the residual amount of dialysate concentrate is not less than the amount of dialysate concentrate provided for the following treatment cycle.

13. Device for supplying a dialysis device with dialysate according to claim 11, characterised in that the arithmetic and evaluation unit (24) is configured in such a way that if the residual amount of dialysate concentrate is greater than the amount of dialysate concentrate provided for the final treatment cycle, a control signal is generated for the dialysis device, by means of which signal the dialysis device is controlled in such a way that the residual amount of dialysate concentrate is completely used up in the final treatment cycle or a specified residual amount of dialysate concentrate remains in the container.

14. Device for supplying a dialysis device with dialysate according to claim 10, characterised in that the arithmetic and evaluation unit (24) is configured in such a way that before the treatment cycles are carried out, the amount ($M_0$) of dialysate concentrate in the container is subdivided among the specified number x of treatment cycles, the treatment cycles each being allocated a specified amount ($V_1', V_2', V_3' \ldots V_x'$) of dialysate concentrate that is set in such a way that, after the treatment cycles have been carried out, a specified residual amount or no residual amount of dialysate concentrate remains in the container.

15. Device for supplying a dialysis device with dialysate according to claim 14, characterised in that the arithmetic and evaluation unit (24) is configured in such a way that a control signal is generated for the dialysis device, by means of which signal the dialysis device is controlled in such a way that the amount ($V_1'$) of dialysate concentrate specified for the first treatment cycle is used up.

16. Device for supplying a dialysis device with dialysate according to claim 15, characterised in that the arithmetic and evaluation unit (24) is configured in such a way that after the first treatment cycle has been carried out using the amount of dialysate concentrate specified for the first treatment cycle and before the start of each subsequent treatment cycle using the amount of dialysate concentrate specified for each of the subsequent treatment cycles, the amount ($V_{actual}$) of dialysate concentrate actually used up in the preceding treatment cycle is determined, the residual volume of dialysate concentrate available for the treatment cycles still to be carried out is calculated from the difference between the amount of dialysate concentrate in the container before the preceding treatment cycle was carried out and the amount of dialysate concentrate actually used up in the preceding treatment cycle, and the residual volume of dialysate concentrate available for each of the treatment cycles still to be carried out is subdivided among the number of treatment cycles still to be carried out, the treatment cycles each being allocated a specified amount $V_1''$, $V_2''$, $V_3''$ ... $V_x''$ of dialysate concentrate that is set in such a way that, after the treatment cycles have been carried out, a specified residual amount or no residual amount of dialysate concentrate remains in the container.

17. Device for supplying a dialysis device with dialysate according to claim 16, characterised in that the arithmetic and evaluation unit (24) is configured in such a way that an alarm signal for generating an alarm is generated if the residual volume of dialysate concentrate available for each of the treatment cycles still to be carried out is less than the amount of dialysate concentrate specified for the treatment cycles still to be carried out, and a control signal for initiating the following treatment cycle is generated if the residual volume of dialysate concentrate available for each of the treatment cycles still to be carried out is not less than the amount of dialysate concentrate specified for the treatment cycles still to be carried out.

18. Device for supplying a dialysis device with dialysate according to claim 10, characterised in that the treatment cycle comprises a preparation phase, preceding the dialysis treatment, for preparing the dialysis treatment and a treatment phase for carrying out the dialysis treatment, the amount of dialysate concentrate provided for one treatment cycle comprising a specified amount of dialysate concentrate for the preparation phase and a specified amount of dialysate concentrate for the treatment phase.

19. Device for supplying a dialysis device with dialysate according to claim 10, characterised in that the container is a bag or cartridge, the volume of the bag or cartridge being set in such a way that the bag or cartridge holds an amount of dialysate concentrate sufficient for a specified number (x) of treatment cycles.

20. Dialysis device comprising a device for supplying the dialysis device with dialysate according to claim 10.

* * * * *